(12) United States Patent
Hamed

(10) Patent No.: US 6,844,066 B2
(45) Date of Patent: Jan. 18, 2005

(54) SUPERABSORBENT CELLULOSIC FIBER AND METHOD OF MAKING SAME

(75) Inventor: Othman A. Hamed, Jesup, GA (US)

(73) Assignee: Rayonier Products and Financial Services Company, Jesup, GA (US)

(*) Notice: Subject to any disclaimer, the term of this patent is extended or adjusted under 35 U.S.C. 154(b) by 0 days.

(21) Appl. No.: 10/440,360

(22) Filed: May 19, 2003

(65) Prior Publication Data

US 2004/0234760 A1 Nov. 25, 2004

(51) Int. Cl.[7] .......................... D01F 3/00; A61F 13/20; D06M 23/00; D02G 3/00
(52) U.S. Cl. ....................... 428/393; 8/116.1; 8/115.51; 604/358; 604/374
(58) Field of Search .................................. 428/364, 375, 428/393; 8/116.1, 115.51; 604/358, 374

(56) References Cited

U.S. PATENT DOCUMENTS

| | | | |
|---|---|---|---|
| 2,757,150 A | 7/1956 | Heritage | |
| 3,656,884 A | * 4/1972 | Okaya et al. | ................ 8/116.1 |
| 3,669,103 A | 6/1972 | Harper et al. | |
| 3,670,731 A | 6/1972 | Harmon | |
| 4,160,059 A | 7/1979 | Samejima | |
| 4,410,571 A | 10/1983 | Korpman | |
| 4,584,357 A | 4/1986 | Harding | |
| 4,600,462 A | 7/1986 | Watt | |
| 4,673,402 A | 6/1987 | Weisman et al. | |
| 4,676,784 A | 6/1987 | Erdman et al. | |
| 4,833,222 A | 5/1989 | Siddall et al. | |
| 5,002,814 A | 3/1991 | Knack et al. | |
| 5,057,166 A | 10/1991 | Young, Sr. et al. | |
| 5,281,207 A | 1/1994 | Chmielewski et al. | |
| 5,669,894 A | 9/1997 | Goldman et al. | |
| 6,068,620 A | 5/2000 | Chmielewski | |
| 6,500,947 B1 | 12/2002 | West et al. | |

* cited by examiner

*Primary Examiner*—N. Edwards
(74) *Attorney, Agent, or Firm*—Hunton & Williams (57) ABSTRACT

The present invention relates to superabsorbent cellulose fiber including cellulose and at least one ethylenically unsaturated monomer. The invention also relates to a method of producing the superabsorbent fiber, and absorbent articles including the superabsorbent fiber.

39 Claims, 3 Drawing Sheets

SUPERABSORBENT CELLULOSIC FIBER AND METHOD OF MAKING SAME

FIELD OF THE INVENTION

The present invention relates to a cellulose-based fiber having superabsorbent properties that can be used in personal care products. The invention further comprises a method of making the fiber. The fiber of the present invention can be obtained by grafting a water-soluble ethylenically unsaturated monomer onto cellulosic fibers in an aqueous medium in the presence of a cross-linking agent and a free radical initiator.

DESCRIPTION OF RELATED ART

Absorbent articles intended for personal care, such as adult incontinent pads, feminine care products, and infant diapers typically are comprised of at least a top sheet, a back sheet, an absorbent core disposed between the top sheet and back sheet, and sometimes an acquisition layer disposed between the top sheet and the absorbent core. The absorbent core typically includes a mixture of fibrous materials and superabsorbent particles. Such superabsorbent polymers usually are capable of absorbing and retaining liquid 10–100 times or more their own weight. Thus, the introduction of superabsorbent material into absorbent products allows for the use of less wood fluff pulp, accordingly smaller and thinner absorbent products are assembled.

Superabsorbent polymers are available in a variety of chemical forms including natural-based polymer and synthetic polymers. Natural-based polymers include for example agar, caboxyalkyl cellulose, gum, pectin, carboxyalkyl starch, cellulose sulfate, and hydrolysis product of starch acrylonitrile graft polymers. Synthetic polymers include for example polyacrylates, sulfonated polystyrene, polyvinyl alcohol, polyetheylene oxides, polyvinylpyrolidine, polycrylonitriles, polyacrylamide, and hydrolyzed polyacrylamide. While such natural-based absorbent materials are known for use in personnel care products, they have not gained wide usage in such products, because their absorbent properties are generally lower than those of synthetic absorbent materials, such as for example sodium polyacrylate. The relatively high cost of these materials has also hindered their use in consumer absorbent products. Furthermore, natural based superabsorbent materials tend to form soft, gelatinous masses when swollen with liquid. The presence of such gelatinous masses in absorbent products tends to limit liquid transport and distribution within the absorbent article. This phenomenon is known as gel blocking. Gel blocking refers to the situation wherein the particles of superabsorbent material deform during swelling and block the interstitial spaces between particles thus preventing the flow of liquid. Once gel blocking occurs, the product cannot efficiently absorb subsequent insult of liquid, and the absorbent article tends to leak.

In contrast to the natural-based absorbent polymer, synthetic superabsorbent polymers often are capable of absorbing large quantities of liquid while maintaining relatively high gel strength. Accordingly, the synthetic superabsorbent material can be incorporated into absorbent articles while minimizing the possibility for gel blocking. The high gel strength (upon swelling) of common synthetic SAP particles helps them to retain a lot of void space between particles, which is helpful for rapid fluid uptake. This high void volume, however, simultaneously results in increased interstitial (between particle) liquid in the product in the saturated state. When there is a surplus of interstitial liquid, the rewet value or wet feeling of an absorbent product is compromised.

Synthetic superabsorbent polymers typically are provided in the form of particulate powders, granules, or fibers that are distributed throughout absorbent cellulosic products to increase the absorbency of the product. Superabsorbent particles are generally discussed, for example, in U.S. Pat. Nos. 4,160,059; 4,676,784; 4,673,402; 5,002,814; and 5,057,166; 5,669,894; and 5,559,335. Absorbent articles such as diapers that incorporate superabsorbent hydrogels are described in, for example, U.S. Pat. Nos. 3,669,103 and 3,670,731.

Synthetic superabsorbent materials typically employed in absorbent products generally are prepared in a two step process. In the first step, ethylenically unsaturated monomer is polymerized using a free radical initiator, and then surface cross-linked in a separate step. Thus, a two step process is involved which make the process technically difficult and expensive.

Several other disadvantages accompany synthetic superabsorbent polymers, such as non-biodegradability. In addition, the amount of superabsorbent material that can be contained within the fiber matrix of the absorbent article should not exceed a certain limit. If the limit is exceeded, the absorbent material tends to physically dislodge from the cellulosic fibers during manufacturing and transportation. Separation of the superabsorbent material from the fiber reduces the absorbency of the product and diminishes the effectiveness of the superabsorbent material. Also when the amount of superabsorbent material exceeds a given limit, the core might fail to function properly due to the absence of significant liquid wicking and distribution of acquired liquid through the storage layer of the absorbent article. Moreover, such absorbent core also might lack enough strength to retain its dry structure, shape and integrity.

Synthetic superabsorbent fibers have been developed in order to overcome these problems. However, the fibers have ended up with several significant obstacles, such as for example, superabsorbent fibers are difficult to process compared to cellulosic fibers, they have poor absorbency under load, poor tensile strength, and the cost of this fiber is significantly higher than superabsorbent particles. As a consequence, superabsorbent polymer fibers have not been used to any significant extent in absorbent products.

Other scientists in the field have attempted to overcome the dislodging of superabsorbent particles from the cellulosic fibers in the absorbent core by attaching the superabsorbent particles to the fiber. A method of attaching superabsorbent particles is disclosed in U.S. Pat. No. 4,410,571 in which a water swellable absorbent polymer is converted to a non-particulate immobilized confluent layer. Polymer particles are converted to a coated film by plasticizing them in a polyhydroxy organic compound such as glycerol, ethylene glycol, or propylene glycol. The superabsorbent assumes a non-particulate immobilized form that can be foamed onto a substrate. The individual particulate identity of the superabsorbent polymer is lost in this process. The coalescent nature of the superabsorbent material also can result in gel blocking, in which absorption is diminished as the water swollen polymers block liquid passage through the film layer.

Numerous other patents have described methods of attaching superabsorbent particles to fibers. Examples include U.S. Pat. No. 2,757,150; U.S. Pat. No. 4,584,357; and U.S. Pat. No. 4,600,462. In general, the methods of attaching superabsorbent polymers to fibers suffer from several obstacles, including generating an increased amount of waste particulates during the attachment process, and excessive dislodging some of the particles from the fibers due to handling of the fibers during shipment.

Modified cellulosic materials in the fiber form having superabsorbent properties are known in the art and described in several patents, for instance U.S. Pat. No. 6,500,947 describes a method of making superabsorbent polymer in the fiber from by sulfonation of the cellulosic fibers. The sulfonation is carried out in an organic solvent using a large proportion of sulfuric acid. It is known that the cellulose fibers' backbone undergoes hydrolysis by sulfuric acid, and as a result of that, sulfated fibers tend to be short with high contents of fines. In addition to that, sulfated fibers tend to form soft, gelatinous masses when swollen with liquid, which makes the fiber unsuitable for use in absorbent articles intended for body waste management.

There is a need for a fibrous absorbent material having a superabsorbent polymer chemically attached to it with absorbent capacity similar to the absorbent capacity for synthetic absorbent fibers. A need also exists for a superabsorbent material in the fiber form that combines the advantages of liquid absorbent capacity of conventional superabsorbent polymers and the advantageous liquid distribution properties of cellulosic fibers. Moreover, there exists a need for a superabsorbent fiber based on biodegradable and renewable starting materials.

The description herein of certain advantages and disadvantages of known cellulosic superabsorbent fibers, and methods of their preparation, is not intended to limit the scope of the present invention. Indeed, the present invention may include some or all of the methods and chemical reagents described above without suffering from the same disadvantages.

SUMMARY OF THE INVENTION

There is a need for a cellulosic based superabsorbent fiber that offers the advantages afforded by conventional superabsorbent fiber based on petrochemicals. There is a particular need for cellulosic based superabsorbent fibers that do not form soft gelatinous masses when hydrated, have good absorbent properties. A need also exists for a simple, convenient and inexpensive method for making such fibers. Moreover there is a need to provide an absorbent article that includes an absorbent core utilizing superabsorbent fiber based on renewable agricultural material.

It would be desirable to provide cellulosic fibrous materials having a superabsorbent polymer covalently coupled to it, that exhibits exceptional liquid absorption and retention properties, especially with respect to salt containing liquid. Also it would be desirable to provide superabsorbent material in the fiber form that combines the advantages of liquid absorbent capacity of conventional superabsorbent polymers and the liquid distribution properties of cellulosic fibers.

Embodiments of the present invention set out to satisfy these needs and other needs readily apparent to those skilled in the art. For example, an embodiment of the invention provides superabsorbent fibers made from renewable and biodegradable natural products, whereby the fibers provide absorbency under load and gel strength comparable to commercially available synthetic superabsorbent fibers. Furthermore, the superabsorbent fibers of the present invention show a superior rate of absorbency.

One aspect of the present invention concerns a method of making superabsorbent cellulosic fibers, wherein an ethynically unsaturated monomer containing at least one acidic group is grafted in the presence of a cross-lining agent onto the cellulosic fibers at high consistency. One preferred embodiment of such a method comprises:

preparing an aqueous solution comprising an ethylenically unsaturated monomer containing at least one acidic group, and cross-linking agent;

contacting the cellulosic fibers and the aqueous solution;

treating the fiber while under an inert atmosphere with free radical initiator; and recovering the grafted cellulosic fiber.

In accordance with a feature of an embodiment of the invention, there is provided a method of grafting a water-soluble ethylenically unsaturated monomer onto cellulosic fibers in the presence of an effective amount of cross-linking agent with a grafting efficiency of more than about 75%.

In accordance with another feature of an embodiment of the invention, there is provided an absorbent core and an absorbent article intended for body waste management that include the superabsorbent fibers for the present invention.

The superabsorbent fibers of various embodiments of the invention differ from the conventional synthetic superabsorbent fibers in that they are based on renewable and biodegradable raw materials, and they are more porous. The enhanced porosity assists in decreasing gel blocking and enhancing the rate of absorbency. The superabsorbent fibers of embodiments of the invention also have higher efficient grafting of ethylenically unsaturated monomers which remain grafted to the cellulosic backbone even after washing.

In accordance with a feature of an embodiment of the invention, there is provided a superabsorbent fiber comprising cellulose and at least one ethylenically unsaturated monomer grafted to the cellulose. It is preferred that the superabsorbent fiber has a grafting efficiency of water-soluble ethylenically unsaturated monomer of more than about 75%.

In accordance with another feature of an embodiment of the invention, there is provided a superabsorbent fiber comprising cellulose and at least one ethylenically unsaturated monomer, whereby the superabsorbent fiber, when incorporated into an absorbent core, provides an absorbent core having a third insult acquisition time of less than about 25 seconds.

In accordance with another feature of an embodiment of the invention, there is provided a superabsorbent fiber comprising cellulose and at least one ethylenically unsaturated monomer, whereby the superabsorbent fiber has an absorbent retention efficiency of from about 0.65 to about 0.99, the absorbent retention efficiency being represented by the following equation:

Absorbent retention efficiency (%)=Absorbency Under Load/Retention Under Load×100.

In accordance with another feature of an embodiment of the invention, there is provided a superabsorbent fiber comprising cellulose and at least one ethylenically unsaturated monomer, whereby the superabsorbent fiber, when incorporated into an absorbent core, provides a core having an absorbency efficiency of from about 0.56 to about 0.95, the absorbency efficiency being represented by the following equation:

Absorbent efficiency (%)=Absorbency Under Load/Absorbent Capacity×100.

These and other features and advantages of the invention will be readily apparent from the following description of the preferred embodiments of the invention.

DETAILED DESCRIPTION OF THE PREFERRED EMBODIMENTS

The present invention is directed to superabsorbent cellulosic fibers, to absorbent materials containing the fibers, and to methods of making the fibers. The superabsorbent cellulosic fibers preferably have improved grafting efficiency-preferably on the order of greater than about 75%, cross linking density of less than about 20%, a free swell capacity of greater than about 10 g/g synthetic saline per gram of fiber, and a centrifuge retention capacity of greater than about 4.0 g/g of synthetic saline per gram of fiber. The method includes coating ethylenically unsaturated monomers containing an acid group onto a cellulosic fiber, and exposing the fiber to an initiator capable of initiating a graft co-polymerization reaction on the fiber surface by generating reactive free radical sites on the surface of the fiber. Thus the free radical sites graft the monomers onto the fiber by forming covalent bonding at reactive sites of the fiber surface.

As used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

As used herein, the terms "absorbent garment," "absorbent article" or simply "article" or "garment" refer to mechanisms that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

The present invention may be used with all of the foregoing classes of absorbent garments, without limitation, whether disposable or otherwise. Some of the embodiments described herein provide, as an exemplary structure, a diaper for an infant, however this is not intended to limit the claimed invention. The invention will be understood to encompass, without limitation, all classes and types of absorbent garments, including those described herein.

The term "component" can refer, but is not limited, to designated selected regions, such as edges, corners, sides or the like; structural members, such as elastic strips, absorbent pads, stretchable layers or panels, layers of material, or the like. Throughout this description, the term "disposed" and the expressions "disposed on," "disposed above," "disposed below," "disposing on," "disposed in," "disposed between" and variations thereof are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

The present invention concerns superabsorbent cellulosic fibers that are useful in absorbent articles, and in particular, that are useful in forming absorbent cores or acquisition layers in the absorbent article. The particular construction of the absorbent article is not critical to the present invention, and any absorbent article can benefit from this invention. Suitable absorbent garments are described, for example, in U.S. Pat. Nos. 5,281,207, and 6,068,620, the disclosures of each of which are incorporated by reference herein in their entirety including their respective drawings. Those skilled in the art will be capable of utilizing the superabsorbent fibers of the present invention in absorbent garments, cores, acquisition layers, and the like, using the guidelines provided herein.

The superabsorbent cellulosic fibers in accordance with the invention preferably possess characteristics that are desirable in absorbent articles. For example, the superabsorbent fibers preferably have a grafting efficiency of greater than about 75%, more preferably greater than about 85% and most preferably greater than about 95%. The grafting efficiency is a measure of how efficient the ethylenically unsaturated monomers were grafted to the cellulosic material. The superabsorbent fibers of the invention also preferably have a cross-linking density of less than about 20%.

The superabsorbent fibers of the invention also can be used in an absorbent core in such a manner that the absorbent core has a third insult acquisition time of less than about 25 seconds. Preferably, the absorbent core containing the superabsorbent fiber of the invention has a third insult acquisition time of less than about 22.5 seconds, more preferably less than about 20 seconds, even more preferably less than about 19 seconds, even more preferably less than about 16.5 seconds, and most preferably less than about 15 seconds.

The superabsorbent fiber of the invention also preferably has an absorbent retention efficiency of from about 0.65 to about 0.99, the absorbent retention efficiency being represented by the following equation:

Absorbent retention efficiency (%)=Absorbency Under Load/Retention Under Load×100.

Preferably, the absorbent retention efficiency is from about 0.70 to about 0.99, more preferably from about 0.75 to about 0.98, and most preferably from about 0.8 to about 0.96.

The superabsorbent fibers of the invention also can be used in an absorbent core in such a manner that the absorbent core has an absorbency efficiency of from about 0.56 to about 0.95, the absorbency efficiency being represented by the following equation:

Absorbent efficiency (%)=Absorbency Under Load/Absorbent Capacity×100.

Preferably, the absorbency efficiency is from about 0.57 to about 0.90, more preferably from about 0.57 to about 0.80, and most preferably from about 0.58 to about 0.75.

The superabsorbent cellulosic fibers of the invention also preferably have a centrifuge retention capacity of greater than about 4 grams of synthetic saline per gram of fiber (hereinafter "g/g"), and preferably more than about 6 g/g. The centrifuge retention capacity measures the ability of the fiber to retain fluid against a centrifugal force. In addition, the superabsorbent cellulosic fiber has desirable properties, such as a free swell of greater than about 10 g/g. The free swell measures the ability of the fiber to absorb fluid without being subjected to a confining or restraining pressure. The free swell preferably is determined by the Teabag method described herein. The particular characteristics of the superabsorbent cellulosic fibers of the invention are determined in accordance with the procedures described in more detail in the examples.

The cellulosic fiber made in accordance with the present invention preferably has a fibrous structure identical to the cellulosic fiber from which it is derived. Moreover the fiber of the present invention is water swellable, water insoluble has high absorbent capacity, high rate of absorbency, and high rate of expansion. The fibers of the present invention preferably are prepared by a process that includes suspending the fiber in an aqueous solution of ethylenically unsaturated monomers, and preferably ethylenically unsaturated monomers containing at least one acid group. The suspension also preferably includes a cross-linking agent or a mixture of cross-linking agents. After mixing the above-described components together, the fiber preferably is pressed to remove excess solution and provide a consistency of more than 15%. The cellulosic fiber then can be graft polymerized by treating it with a free radical initiator preferably in a deoxygenated atmosphere.

As used herein, the term "consistency" refers to the concentration of cellulosic fibers in a mixture. As such, the consistency represents the weight of cellulosic fibers present in a mixture divided by the total weight of the mixture multiplied by 100. The consistency is presented herein by a weight percent.

The process of the present invention results in a number of advantages over known processes. For example, the inventive process permits the production of grafted cellulosic fibers using low amounts of water (i.e., high consistency). In addition, in a most preferred embodiment of the invention, the inventive process allows grafting of water-soluble monomers such as acrylic acid with more than 95% grafting efficiency. As used herein, the terms "grafting efficiency" refer to the percent weight of the ethylenically unsaturated monomer that can't be washedout from the fiber after grafting. As such, the grafting efficiency is determined in accordance with the following equation:

$$\% \text{ Grafting Effeciency} = \frac{\text{Dry weight of grafted fiber} - \text{Dry weight of orginal fiber}}{\text{Weight of ethynically unstaurated monomer}} \times 100$$

Suitable cellulosic fibers for use in forming the high absorbent fiber of the present invention include those primarily derived from wood pulp. Suitable wood pulp can be obtained from any of the conventional chemical processes, such as the Kraft and sulfite processes, with or without subsequent bleaching. Preferred fibers are those obtained from various soft wood pulp such as Southern pine, White pine, Caribbean pine, Western hemlock, various spruces, (e.g. Sitka Spruce), Douglas fir or mixtures and combinations thereof. Fibers obtained from hardwood pulp sources, such as gum, maple, oak, eucalyptus, poplar, beech, and aspen, or mixtures and combinations thereof also can be used in the present invention. Other cellulosic fiber derived form cotton linter, bagasse, kemp, flax, and grass also may be used in the present invention. The fiber can be comprised of a mixture of two or more of the foregoing cellulose pulp products. Particularly preferred fibers for use in forming the superabsorbent fibers of the present invention are those derived from wood pulp prepared by the Kraft and sulfite-pulping processes.

Figure 1:
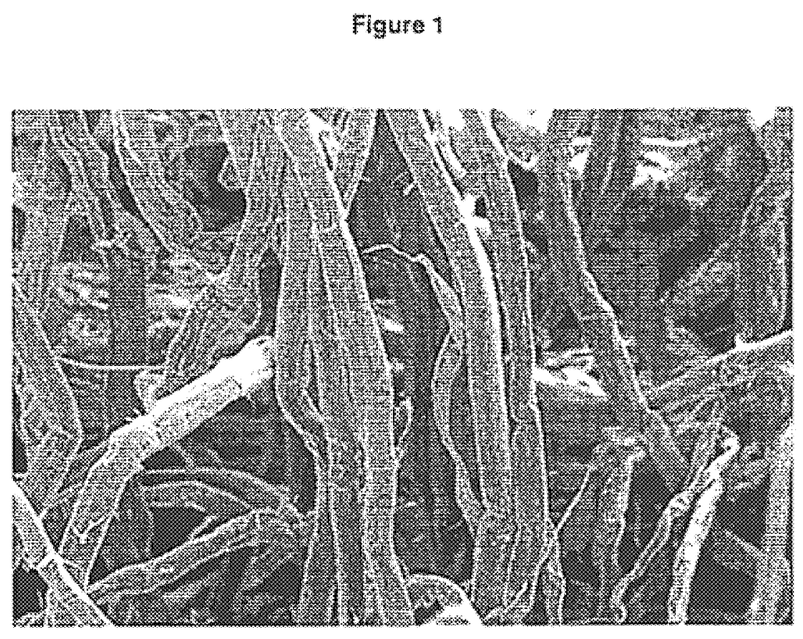
FIG. 1 is a scanning electron microscope (SEM) photograph of mercerized fiber at 200× magnification.

In another aspect of the invention, suitable fibers for use in the present invention include refined and caustic treated cellulosic fibers, or "mercerized fiber." A scanning electron microscsope (SEM) photograph of a mercerized fiber at 200× magnification is shown in FIG. 1. Caustic treatment can be carried out by any method known in the art, such as those described in *Cellulose and Cellulose Derivatives*, Vol. V, Part 1, Ott, Spurlin, and Graflin, eds., Interscience Publisher (1954). Caustic treatment of pulp can be carried out by mixing pulp in an aqueous solution of alkali metal, such as sodium hydroxide, washing, neutralizing or washing and neutralizing, and optionally drying the pulp.

The caustics used in the caustic treatment serve to extract residuals such as lignin and hemicellulose that may be left on the pulp after the pulping and bleaching processes. In addition, treatment with caustic solution at specific concentrations is capable of converting cellulose from its native structure form, cellulose 1, to a more thermodynamically stable and less crystalline form cellulose 11 in which the hydroxyl groups are more accessible to chemicals.

Reagents suitable for caustic treatment include, but are not limited to, alkali metal hydroxides, such as sodium hydroxide, potassium hydroxide, calcium hydroxide, and rubidium hydroxide, lithium hydroxides, and benzyltrimethylammonium hydroxides. Sodium hydroxide is a particularly preferred reagent for use in the caustic treatment to produce cellulosic fibers suitable for forming the superabsorbent cellulosic fibers in accordance with the present invention. The pulp preferably is treated with an aqueous solution containing from about 4 to about 30% by weight sodium hydroxide, (or any other suitable caustic material), more preferably from about 6 to about 20%, and most preferably from about 12 to about 16% by weight, based on the weight of the solution. Caustic treatment may be performed during or after bleaching, purification, and drying. Preferably, the caustic treatment is carried out during the bleaching and/or drying process.

It is preferred in the present invention that the caustic treatment be carried out at or about room temperature. Those skilled in the art will be capable of treating the fibers with caustic at a suitable temperature using the guidelines provided herein. After caustic extraction, the cellulose fiber can be of any purity, and preferably is of high cellulose purity, containing more than 65% by weight of α-cellulose.

Commercially available caustic extractive pulp suitable for use in the present invention include, for example, Porosanier-J-HP, available from Rayonier Performance Fibers Division (Jesup, Ga.), Buckeye's HPZ, available from Buckeye Technologies (Perry, Fla.), and TRUCELL available from Weyerhaeuser company (Federal Way, Wash.).

The ethylenically unsaturated monomers of the present invention preferably should be selected so as to accomplish desired graft polymerization reaction and capable of providing fiber with desirable properties. Preferably, the ethylenically unsaturated monomer suitable for use in the present invention are those that contain a moiety of the following formula:

and which undergo free radical polymerization. More specifically, the ethylenically unsaturated monomer may comprise an acrylic monomer, an acryl-amide, a methacrylamid, acrylonitrile, a vinyl-substituted heterocyclic compound, or mixtures thereof.

It is preferred in the present invention that the ethylenically unsaturated monomer contain at least one acid group. Suitable ethylenically unsaturated monomer containing at least one acid group are acrylic monomers having the general formula:

where R represents hydrogen, methyl, or ethyl. Particularly preferred ethylenically unsaturated monomers include, for example, acrylic acid, methacrylic acid, ethacrylic acid, α-chloroacryiic acid, α-cynoacrylic acid, vinylysulfonic acid, acryamidopropanesulfonic acid, crotonic acid, α-acryloxypropionic acid, sorbic acid, isocrotonic acid, itaconic acid, alkali metal salts and ammonium salts, and mixtures thereof.

The ethylenically unsaturated monomer may further comprise an acrylamide or a methacrylamide moiety. Such monomers also are well known in the art and include such specific compounds as acrylamide, methacrylamide, N-methylacrylamide, N-ethylacrylamide, N-isopropylacrylamide, diacetone acrylamide, N-methylol acrylamide, the corresponding methacrylamides, 2-acrylamide-2-methyl-1-propane sulfonic acid and its salts, vinyl phosphoric acid and its salt, and the like. Acrylonitrile also is suitable for use as an ethylenically unsaturated monomer.

The more preferred ethylenically unsaturated monomers include acrylic acid, methacrylic acid, ethacrylic acid, α-chloroacrylic acid, α-cynoacrylic acid, crotonic acid, α-acryloxypropionic acid, sorbic acid, isocrotonic acid and alkali metal salts and ammonium salts thereof; itaconic acid, acrylamide, methacrylamide and 2-acrylamido-2-methyl-1-propane sulfonic acid and its salts.

Specially preferred acrylic monomers are acrylic acid, methacrylic acid, their respective salt forms such as alkali metal or ammonium salts, and mixtures thereof.

To improve the properties of the fiber, it is preferred to use an additional hydrophobic ethylenically unsaturated monomer that is capable of copolymerizing with the hydrophilic ethylenically unsaturated monomer. These hydrophobic monomers can be added to the reaction mixture in amounts within the rang from about 0 to about 20% by weight, preferably not more than about 15%, more preferably not more than about 10%, and most preferably not more than about 5%. Examples of the hydrophobic monomers that are suitable for use in the present invention include, but are not limited to methyl acrylate, ethyl acrylate, hydroxyethyl acrylate, phenoxyethyl acrylate, propyl acrylate, butyl acrylate, 2-ethylhexyl acrylate, glycidyl acrylate, ethylene glycol diacrylate, diethylene glycol diacrylate, 1,6-hexanediol diacrylate, trimethylolpropane triacrylate, pentaerythritol triacrylate, pentaerythritol tetraacrylate, methyl methacrylate, ethyl methacrylate, hydroxyethyl methacrylate, dimethylaminoethyl methacrylate, propyl methacrylate, butyl methacrylate, 2-ethylhexyl methacrylate, glycidyl methacrylate, ethylene glycol dimethacrylate, diethylene glycol dimethacrylate, triethylene glycol dimethacrylate, tetraethylene glycol dimethacrylate, trimethylolpropane trimethacrylate, bisphenol A dimethacrylate, and mixtures thereof.

Preferred acrylate monomers for use in the present invention include methyl acrylate, ethyl acrylate, propyl acrylate, butyl acrylate, 2-ethylhexyl acrylate, methyl methacrylate, ethyl methacrylate, propyl methacrylate, butyl methacrylate, 2-ethylhexyl methacrylate, and mixtures thereof.

The grafting may be carried out using acid monomers that are not neutralized or that have been neutralized or partially neutralized prior to mixing with fiber. Preferably the acid monomers used in the grafting process are not neutralized. While not intending on being bound by any theory, the inventor discovered that neutralized acrylic acid exhibited a lower tendency for grafting and led to a product with low grafting efficiency. If the ethylenically unsaturated monomers are neturalized, it is preferred that the neutralization be achieved by contacting the aqueous monomer with an amount of basic material sufficient to neutralize between about 20 and about 95 percent of the acid groups present in the acid monomers. Preferably, the amount of basic material will be sufficient to neutralize between about 40 percent and 85 percent, and most preferably between about 55 percent and about 75 percent of the acid groups present in the acid monomers.

Compounds that are useful to neutralize the acid groups of the monomer are typically those that will sufficiently neutralize the acid groups without having a detrimental effect on the polymerization process. Examples of such compounds include alkali metal hydroxides, and alkali metal carbonates and bicarbonates. Preferably, sodium or potassium hydroxides or carbonates are employed to neutralize the monomer. In determining the desired degree of neutralization, care typically is taken to ensure that the pH of the resulting grafted fiber, which will be contacted with or dispersed in an aqueous fluid to be absorbed, is maintained in a range appropriate for the applications for which the fiber is intended. Preferably, the grafting is carried out employing unneutralized monomers and thereafter neutralizing, as is known in the art.

The amount of monomers present in the reaction mixture can be any amount suitable to form fibers having superabsorbent properties, as well as other desirable properties described herein. It is preferred that the amount of monomers used in the present invention be within the range of from about 5% to about 50% by weight, based on the total weight of the reactants. Preferably, the amount of monomers used in the invention is within the range of from about 10% to about 50%, and more preferably from about 15% to 40% by weight, based on the total weight of the reactants.

It is preferred in the invention that the cellulosic fiber is grafted with the ethylenically unsaturated monomer in the presence of a free radical initiator. Suitable free radical initiators for use in the present invention include, for example, water soluble persulfates such as potassium persulfate, ammonium persulfate, sodium persulfate, and other alkali-metal persulfates, hydrogen peroxide, ammonium cerium nitrate, and water soluble azo-compounds such as 2,2'-azobis-(2-amidinopropane) hydrochloride may be used. Some of these initiators, such as hydrogen peroxide, can be combined with reducing substances such as iron, sulfites, or amines to form known redox type initiators necessary to initiate the grafting reaction. These initiators can be used in the form of a mixture of two or more thereof. Persulfates and ammonium cerium nitrate are particularly preferred initiators for use in the present invention.

The total amount of initiators used may range anywhere from about 0.01 to about 1.0 weight percent, preferably from about 0.01 to about 0.5 weight percent, based on the total weight of the cellulosic fiber and ethylenically unsaturated monomer.

In order to increase fiber absorbency under load and to minimize the formation of homopolymer it is preferred that the cellulosic fibers are reacted with ethylenically unsaturated monomer in the presence of cross-linking agent. Preferably the fiber has a cross-linking density, (which is related to the degree of cross-linking or how much cross-linking has taken place) of less than about 15%, more preferably less than 10%, and most preferably between 0.05% and 5%.

The crosslinking agent preferably is present in an amount effective to covalently cross-link the water-soluble ethylenically unsaturated monomer and cellulosic fiber. The preferred amount of crosslinking agent can be determined based on the desired degree of absorption capacity and the desired strength to retain the absorbed fluid, (i.e., the desired absorption under load (AUL). The crosslinking agent may be used in amount that affords the fiber with desirable cross-linking density mentioned herein. Preferably the cross-linking agent is used in an amount ranging from about 0.05 to about 5 wt %, based on the total weight of the monomer and the fiber. More preferably, the amount of crosslinking agent ranges from about 0.1 to about 1 wt %, based on the total weight of the monomer and fiber. Usually, if the crosslinking agent is used in an amount over about 5 wt %, the resulting fiber may have too high a crosslinking density and may exhibit a reduced absorption capacity and increased strength to retain the absorbed fluid. On the other hand, if the crosslinking agent is used in an amount less than about 0.05 wt %, the grafted fiber may have too low a crosslinking density, and when contacted with the fluid to be absorbed, may become sticky and exhibit a lower initial absorption rate and low absorbency under load. Using the guidelines provided herein, those skilled in the art will be capable of determining a suitable amount of cross-linking agent to employ in the invention.

The desired crosslinking may be achieved by reacting the cellulosic fiber and the water-soluble ethylenically unsaturated monomer in the presence of a crosslinking agent. Cross-linking agents suitable for use in the present invention include those have polyfunctional groups able to polymerize in the presence of a free radical initiator, or those capable of reacting with carboxyl and hydroxyl groups of the neighboring monomers simultaneously.

Polyfunctional cross-linking agent suitable for use in the present invention preferably are selected from the following:

diacrylates and dimethacrylates of ethylene glycol, diethylene glycol, triethylene glycol, propylene glycol, 1,4-butanediol, 1,5-pentanediol, 1,6-hexanediol, neopentyl glycol, trimethylolpropane and pentaerythritol; triacrylates and trimethacrylates of trimethylolpropane and pentaerythritol; highly ethoxylated trimethylol propane triacrylate; tetracrylate and tetramethacrylate of pentaerythritol; allyl methacrylate: and tetraallyloxyethane;

Bisacrylamides such as for example N,N'-methylenebisacrylamide, N,N'-ethylenebismethacrylamide, N-methylolacrylamide, N-methylolmethacrylamide;

Epoxy acrylates such as for example glycidyl acrylate, glycidyl methacrylate, polyethyleneglycol diacrylate, polyethylene glycol dimethacrylate, polypropylene glycol diacrylate, polypropylene glycol dimethacrylate, 3-(acryloyoxy)-2-hydroxypropylmethacrylate, etheylene glycol diacrylate, diethylene glycol diacrylate, triethylene glycol triacrylate, 1,1,1-trimethylolpropane triacrylate, glycerol propyxylatetriacrylate, and triglyceroltriacylate;

Allylamines such as for example di and triallyl amines;

Polyepoxides such as, for example, polyglycidyl ethers, such as, for example, ethylene glycol diglycidyl ether, glycerol triglycidyl ether, glycerol diglycidyl ether, glycerol propoxylate triglycidyl ether, polyethylen glycol diglycidyl ether, propylene glycol glycidyl ether, 1,4-cyclohexanoldimethanol diglycidyl ether, diglycidyl 1,2-cyclohexanedicrboxylate, N,N-diglycidyl aniline, N,N-diglcidyl-4-glycidyloxyaniline, and diglycidyl 1,2,3,4-tetrahydrophthalate;

Epoxy silanes including glycidoxymethyltrimethoxysilane, glycidoxymethyl triethoxysilane, 2-glycidoxyethyl trimethoxysilane, 2-glycidoxyethyltriethoxysilane, 1-glycidoxyethyl trimethoxysilane, 1-glycidoxyethyl triethoxysilane, 3-glycidoxypropyltrimethoxysilane, 3-glycidoxypropyl triethoxysilane, 2-glycidoxypropyl trimethoxysilane, 2-glycidoxypropyltriethoxysilane, 1-glycidoxypropyl trimethoxysilane, 1-glycidoxypropyl triethoxysilane, 4-glycidoxybutyltrimethoxysilane, 4-glycidoxybutyl triethoxysilane, 3-glycidoxybutyl trimethoxysilane, 2-glycidoxybutyltrimethoxysilane, 2-glycidoxybutyl triethoxysilane, 1-glycidoxybutyl trimethoxysilane, 1-glycidoxybutyl triethoxysilane, (3,4-epoxycyclohexyl) methyltrimethoxysilane, (3,4-epoxycyclohexyl) methyl triethoxysilane, glycidoxymethylmethyl dimethoxysilane, glycidoxymethylmethyl diethoxysilane, 2-glycidoxyethylmethyl dimethoxysilan-e, 2-glycidoxyethylmethyl diethoxysilane, 1-glycidoxyethylmethyl dimethoxysilane, 1-glycidoxyethylmethyl diethoxysilane, 3-glycidoxypropylmethyl dimethoxysilane, 3-glycidoxypropylmethyl diethoxysilane, 2-glycidoxypropylmethyl dimethoxysilane, 2-glycidoxypropylmethyl diethoxysilane, 1-glycidoxypropylmethyl dimethoxysilane, 1-glycidoxypropylmethyl diethoxysilane, 4-glycidoxybutylmethyl dimethoxysilane, 4-glycidoxybutylmethyldiethoxysilane, 3-glycidoxybutylmethyl dimethoxysilane, 3-glycidoxybutylmethyl diethoxysilane, 2-glycidoxybutylmethyl dimethoxysilane, 2-glycidoxybutylmethyldiethoxysilane, 1-glycidoxybutylmethyl dimethoxysilane, 1-glycidoxybutylmethyl diethoxysilane, (3,4-epoxycyclohexyl)methylmethyl dimethoxysilane, and (3,4-epoxycyclohexyl)methylmethyldiethoxysilane;

methacryloxy or acryloxy silanes including 2-methacryloxypropyltriethoxysilane, 3-acryloxypropyltrimethoxysilane, 2-acryloxypropyltriethoxysilane, 3-methacryloxypropylmethyldimethoxysilane, 2-methacryloxypropylmethyldiethoxysilane, 3-acryloxypropylmethyldimethoxysilane, 2-acryloxypropylmethyldiethoxysilane, 3-methacryloxypropyltrimethoxysilane, methacryloxypropyltris(methoxyethoxy)methoxysilane;

Aminosilanes including (alkyl)alkoxysilanes having an amino group such as 3-aminopropyltrimethoxysilane, 3-aminopropyltriethoxysilane, N-2-(aminoethyl)-3-aminopropyltriethoxysilane, N-2-(aminoethyl)-3-aminopropylmethyldimethoxysilane, N-phenyl-3-aminopropyltrimethoxysilane, N-(2-aminoalkyl)-3-aminopropyltrimethoxysilane, N-(2-aminoethyl)-3-aminopropyltriethoxysilane, N-(2-aminoethyl)-3-aminopropylmethyldimethoxysilane, 3-aminopropyltriethoxysilane, N-(cyclohexyl)-3-aminopropyltrimethoxysilane, N-(2-aminoethyl)-3-aminopropyl-tris(trimethylsiloxy)silane and 1,2-bis[N-(2-aminoethyl)-3-aminopropyl]-1,1,2,2-tetramethyldisiloxane.

Mixtures and/or blends of these cross-linking agents also may be used.

While the crosslinking agent will typically be soluble in the aqueous solution of the ethylenically unsaturated monomer, the crosslinking agent may be dispersible in such a solution without negative implications. The use of such dispersing agents is disclosed in U.S. Pat. No. 4,833,222, the disclosure of which is incorporated herein by reference in its entirety. Suitable dispersing agents include carboxymethyl cellulose, methylcellulose, hydroxypropyl cellulose, polyvinyl alcohol, and mixtures thereof. Such dispersing agents typically are provided at a concentration between about 0.005 and about 0.1 wt %, based on the total weight of ethylenically unsaturated monomer and fiber In another preferred embodiment, the cellulosic-based superabsorbent fibers of the present invention can be prepared by various methods. In one method, the cellulosic fiber is impregnated in an excess solution of ethylenically unsaturated monomer and cross-linking agent at a consistency of about 6.0%, preferably at a consistency of about 4%. After agitation for about 10 min, preferably 20 min, and most preferably 30 min, excess solution is removed by any manner known in the art. Preferably, excess solution is removed by suction filtration or centrifuge to obtain fibers having a consistency within the range of from about 15% to about 35%. The desired wt % of monomer and cross-linking agent on the fiber can be achieved by using an aqueous solution of monomer and cross-linking agent with a concentration that affords a desirable wt % of monomer and cross-linking agent on fiber based on fiber pick-up. Using the guidelines provided herein, those skilled in the art will be capable of utilizing the appropriate amounts of monomer and cross-linking agents, and contacting them for sufficient periods of time to achieve the desired properties.

It has been discovered that the amount of water present in the reaction mixture may affect the grafting efficiency. For example, it has been discovered that carrying out the grafting method at high consistency results in high grafting efficiency, on the order of greater than 75%, preferably more than 80%, and more preferably more than 90%, and most preferably more than 95%.

Preferably, the grafting reaction is carried out in the presence of water. Other solvents, however, may be used, including glacial acetic acid, and the like. Skilled artisans are capable of carrying out the grafting reaction described herein to effect the desired grafting efficiency and other desirable properties of the superabsorbent fiber (e.g., acquisition time, absorbency efficiency, etc.), using the guidelines provided herein.

Impregnated fiber then can be introduced into a reaction vessel provided with agitation and constructed in a manner that the reaction can be carried out under an inert atmosphere. Suitable reaction vessels include, for example, high Parr reactors (horizontal or vertical), reaction kettles, sigma blades, ribbon blades, pin blades, etc. Preferred reaction vessels include those having a glass or a stainless steel surface. After the air inside the reactor has been displaced with an inert atmosphere, a solution of the free radical initiator preferably is added drop-wise via Teflon tubing, or a syringe to the mixture of fiber, cross-linking agent, and ethylenically unsaturated monomer. When the grafting is conducted in a high Parr reactor, preferably the reaction mixture is degassed by vacuum.

In another embodiment, the cellulosic fiber can be impregnated as described before in an aqueous solution of ethylenically unsaturated monomer and cross-linking agent containing salt having a relatively high solubility in water. Preferably the salt concentration is about 5 wt % based on the total weight of the solution, more preferably about 10%, and most preferably about 20 wt %. Thus, the salt concentration can be anywhere from about 5 to about 20 wt %, based on the total weight of the solution. Including salt in the grafting method allows the grafting co-polymerization to be performed at low consistency without scarifying the grafting efficiency. The consistency can be as low as 5%, and preferably, the consistency is between about 5 and about 10%. Suitable salting agents for use in the present invention include, but are not limited to, sodium, potassium, and ammonium salts.

In another embodiment of the invention, never dried cellulosic fiber with moisture contents of not more than 50% can be introduced into the reactor, and an aqueous solution of the monomer is sprayed onto the fiber. The ethylenically unsaturated monomer and cross-linking agent preferably are added to the cellulosic fiber in an amount that provides the fiber with the desirable properties described herein. Preferably, the ethylenically unsaturated monomer is added in a solution with a concentration that provides the cellulosic fiber with a consistency within the range of from about 15% to about 30%. Preferably, salt is included in the solution, and the salt concentration can be anywhere from about 5 wt % to about 20 wt %, based on the total weight of the solution. When salt is included, the consistency can be anywhere from about 5% to about 30%. After the monomer solution has been added to the cellulosic fiber, the air can be removed from the reactor, and a solution of free radical initiator then can be added. In another embodiment, the solution containing the free radical initiator is applied prior to application of the solution containing the ethylenically unsaturated monomer and cross-linking agent.

Preferably the cellulosic fiber is suspended in an excess solution of ethylenically unsaturated monomer and cross-linking agent before treatment with free radical initiator. Such treatment creates uniform distribution of monomers and provides better penetration of monomers into cellulose crystalline areas and promotes the grafting reaction.

The reaction temperature as well as the reaction period will depend, in part, on the free radical initiator employed, and those skilled in the art are capable of determining a suitable reaction temperature and time using the guidelines provided herein. For example, initiators such as ammonium cerium nitrate typically require no heat to generate free radicals and consequently, the reaction can be performed at room temperature. Preferably the graft polymerization reaction is carried out at a temperature within the range of from about 20 to about 40° C. As an additional example, when persulfate initiators are used, the reaction preferably is carried out at a temperature within the range of from about 50° C. and about 80° C. The reaction preferably is carried for a period of time until the level of the residual monomer is below 5% by weight of the total weight of the solids. In the context of the present invention, the time required for the reaction to be completed, in general, can range anywhere from about 30 minutes to about 120 minutes.

The reaction preferably is carried out under an ambient atmospheric pressure of an inert gas such as nitrogen, argon, helium, neon, and carbon dioxide. However, the reaction also or optionally can be conducted under the impetus of pressure. Preferably, the pressure is less than 150 psi, more preferably less than 100 psi, even more preferably less than 80 psi, and most preferably less than 50 psi. The pressure usually can be anywhere from about 1 psi to 150 psi.

The process can be accelerated be removing any inhibitors that are included with the monomers to prolong monomers shelf life. However, generally it is unnecessary to remove the inhibitors contained in the monomers.

After the reaction has been completed the grafted fiber can be removed from the reactor and neutralized to a pH ranging from about 4 to about 8 using compounds that are useful to neutralize the acid groups of the monomer without having a detrimental effect on the fiber performance. Examples of such compounds include alkali metal hydroxides, alkali metal carbonates, and alkali metal bicarbonates, ammonium hydroxide, and ammonia gas. Preferably, sodium or potassium hydroxide or carbonates thereof are employed to neutralize the monomer. The neutralization preferably is performed using excess water at a consistency of about 6%, preferably at 4%, and most preferably at 3%. After neutralization, the fiber preferably is recovered from the aqueous solution. Any method for recovering the grafted fiber from the aqueous solution without unacceptably negatively affecting the absorption properties of the grafted fiber is acceptable for use in the present invention. Examples of accepted methods include evaporating drying, freezing drying, critical point drying, dehydration using organic solvent, and the like.

As used herein, recovery of the grafted fiber from the aqueous solution is meant to represent that substantially all of the water used in fiber neutralization and, if present, un-reacted monomers and homopolymer are removed from the fiber. Preferably, the grafted fiber is recovered from the aqueous solution by dehydration in which a dehydrating agent such as acetone, methyethylketone, methanol, ethanol, propanol, or isopropyl alcohol is added to the aqueous mixture of the fiber. The dehydrated fiber can then be recovered by suction filtration or centrifuge.

A small amount of water or solvent used in fiber dehydration described before may remain entrapped within the fiber structure of the grafted fiber. Preferably the amount of water remaining in the fiber after recovering the grafted fiber is less than 200 wt % based on the weight of the grafted fiber, more preferably less than 100 wt % of the fiber, and most preferably less than 50 wt % based on the weight of the grafted fiber. Fiber drying then can be carried at room temperature or in an oven, preferably at a temperature below a 100° C.

In another preferred embodiment of the present invention, the superabsorbent fibers of the present invention can be formed into a hand sheet. Such a hand sheet may be formed by either wet-laid or an air laid process. A wet-laid handsheet may prepared as shown in the experimental section by suspending the fiber in an aqueous solution containing water-miscible organic solvents. Suitable water-miscible organic solvents include alcohols and ketones such as methanol, ethanol, propanol, isopropanol, acetone, methylethyl ketone, and mixtures thereof. The sheet then can be either compressed and densified, or it can be made to have a low density (such as, for example, a roll good) for direct use in absorbent articles.

The performance characteristics of the fiber of the present invention can be further improved by surface cross-linking. Surface cross-linking can be carried out in a conventional manner using cross-linking agents capable of reacting with the functional groups of the grafted fibers. Cross-linking agents preferably are applied to the surface of the fiber while in the sheet or fluff form, preferably in the form of an aqueous solution containing water-miscible organic solvents such as for example methanol, ethanol, propanol, isopropanol, acetone, methylethyl ketone, and mixtures thereof.

Suitable surface cross-linking agent include for example:
polyepoxy and silane compounds such as those mentioned before in this patent.

Polyols such as ethylene glycol, glycerol, 1,2-propanediol, 1,4-propanediol, polyethyleneglycol, polyglycerol, pentaerythritol, sorbitol.

Carbonic acid derivatives such as urea, guadine, and dicyanomide.

Particularly preferred surface cross-linking agents are polyepoxides and silanes.

The cross-linker solution preferably is applied on the fiber surface by spraying while the fiber is in the sheet or fluff form, followed by heating the treated fiber in an air forced oven at a temperature of from about 100 to about 220° C., preferably from about 120 to about 200° C., and most preferably from about 140 to about 190° C. for from about 5 to about 30 min.

The cellulosic based superabsorbent fiber of the present invention is characterized by having high degree of structural integrity. As used herein structural integrity relates to the shape, strength, stiffness and resiliency of conventional cellulosic fiber. The fibers of the invention also are notable for having high absorption capacitates, high centrifuge retention, high rate of absorption, and good liquid transportation and wicking properties.

The superabsorbent cellulosic fibers of the present invention preferably have a free swell, as determined in accordance with the test procedure outlined herein, of greater than 10.0 g/g of synthetic saline (0.9% by weight NaCl) per gram fiber. More preferably the free swell is greater than 20.0 g/g and most preferably above 25 g/g. The free swell can be any were from about 8 to about 35 g/g, more preferably from about 10 to about 30 g/g, and most preferably from about 12 to about 25 g/g.

The centrifuge retention capacity of the superabsorbent cellulosic fiber of the present invention, as determined in accordance with the test procedure outlined herein, preferably is greater than 4.0 g/g of synthetic saline (0.9% by weight NaCl) per gram fiber. More preferably, the centrifuge retention capacity is greater than 6.0 gig and most preferably above 10.0 g/g. The centrifuge retention capacity can be any were from about 4.0 to about 13.0 g/g.

The superabsorbent cellulosic fibers prepared in accordance with the present invention can be utilized, for example, as absorbent materials in an absorbent core, or in an acquisition/distribution layer of an absorbent article. These applications typically require good absorbency and porosity. The superabsorbent fibers can be used, for example, in non-woven, fluff absorbent applications. The fibers can be used independently, or incorporated into other cellulosic fibers to form blends using conventional techniques, such as air laying techniques. In an airlaid process, the fibers, alone or combined in blends with other fibers, typically are blown onto a forming screen or drawn onto the screen via a vacuum. Wet laid processes also may be used, combining the superabsorbent fibers of the invention with other cellulosic fibers to form sheets or webs of blends.

The superabsorbent fiber of the present invention can be incorporated into various absorbent articles preferably intended for body waste management such as adult incontinent pads, feminine care products, and infant diapers. Towels and wipes also may be made with the superabsorbent fibers of the present invention, and other absorbent products such as filters. Accordingly, an additional feature of the present invention is to provide an absorbent core, or other component of an absorbent article that includes the superabsorbent fibers of the present invention.

As is known in the art, absorbent cores typically are prepared using fluff pulp to wick the liquid, and an absorbent polymer (oftentimes a superabsorbent polymer (SAP)) to store liquid. As noted previously, the superabsorbent fibers of the present invention have many desirable properties for use in an absorbent core. Furthermore, the superabsorbent fibers of the present invention are highly porous. Accordingly, the superabsorbent fibers of the present invention can be used as a substitute for, or in combination with the SAP to prepare an absorbent composite (or core) having improved porosity, bulk, resiliency, wicking, softness, absorbent capacity, absorbency under load, low third insult strikethrough, high centrifuge retention capacity, and the like. The absorbent composite could be used as an absorbent core of the absorbent articles intended for body waste management.

It is preferred in the present invention that the superabsorbent fibers be present in the absorbent composite in an amount ranging from about 10 to about 80% by weight, based on the total weight of the composite. More preferably, the superabsorbent fibers are present in an absorbent composite from about 20 to about 60% by weight. A mixture of conventional cellulosic fibers and superabsorbent fibers of the present invention along with optional additional SAP also can be used to make the absorbent composite. Preferably, the superabsorbent fibers of the present invention are present in the fiber mixture in an amount from about 1 to 80% by weight, based on the total weight of the fiber mixture, and more preferably present in an amount from about 10 to about 60% by weight. Any conventional cellulosic fiber may be used in combination with the superabsorbent fibers of the invention. Suitable additional conventional cellulosic fibers include any of the wood fibers mentioned previously, caustic treated fibers, rayon, cotton linters, and mixtures and combinations thereof.

Any suitable SAP can be used or other absorbent material, as an optional component to form the absorbent composite, absorbent core, and absorbent article of the present invention. The SAP can be in the form of, for example, fiber, flakes, or granules, and preferably is capable of absorbing several times its weight of saline (0.9% solution of NaCl in water) and/or blood. The SAP also preferably is capable of retaining the liquid when it is subjected to a load. Non-limiting examples of superabsorbent polymers applicable for use in the present invention include any SAP presently available on the market, including, but not limited to, polyacrylate polymers, starch graft copolymers, cross-linked carboxymethylcellulose derivatives, and mixtures and combinations thereof.

An absorbent composite made in accordance with the present invention preferably contains the superabsorbent fiber of the present invention and optional SAP in a total amount of from about 20 to about 60% by weight, based on the total weight of the composite, and more preferably from about 30 to about 60% by weight.

A method of making an absorbent composite of the present invention may include forming a pad of fibers, albeit cellulose or other fibers, or mixtures of the superabsorbent fibers and other fibers, and incorporating the superabsorbent fibers and optional superabsorbent polymer particles in the pad. The pad can be wet laid or airlaid. Preferably the pad is airlaid.

Absorbent cores containing superabsorbent fibers of the invention preferably have dry densities of between about 0.1 g/cm$^3$ and 0.50 g/cm$^3$, and more preferably from about 0.2/cm$^3$ to 0.4 g/cm$^3$. The absorbent core can be incorporated into a variety of absorbent articles, preferably those articles intended for body waste management, such as diapers, training pants, adult incontinence products, feminine care products, and toweling (wet and dry wipes).

While not intending on being limited by any theory of operation, the reaction scheme shown below represents one of the possible mechanisms of the cellulosic fiber reaction with an ethylenically unsaturated monomer containing carboxylic acid groups and cross-linking agent 3-methacryloxypropyltrimethoxysilane. The scheme is provided for the purpose of illustrating, not limiting, the grafting reaction of the present invention.

-continued

To evaluate the various attributes of the present invention, several tests were used to characterize the superabsorbent fibers' performance improvements resulting from the presently described method.

The invention will be illustrated but not limited by the following examples. While the invention has been described with reference to particularly preferred embodiments and examples, those skilled in the art recognize that various modifications may be made to the invention without departing from the spirit and scope thereof.

EXAMPLES

The following test methods were used to measure and determine various physical characteristics of the inventive superabsorbent cellulosic fibers.

Test Methods

The Teabag Method

The Teabag Method is a test method used to measure the absorbent capacity under zero load, or "free swell" of the inventive suberabsorbent cellulosic fiber. In this test, 2.000 g (±0.001 g), dry weight basis, of superabsorbent fiber was placed into a pre-weighed (±0.001 g) cloth teabag whereby the open end of the tea bag that contained the superabsorbent fiber was sealed with an iron. The teabag and contents then were placed in a pan of 0.9% saline solution and allowed to soak for 30 minutes. The teabag then was removed from the solution, hanged on a drip rack, and allowed to drip dry for 10 minutes. The teabag and contents were weighed and the amount of solution retained in the fibers was determined. A teabag containing no fibers was run under similar conditions, and served as a blank. The results were used to calculate the amount of saline in grams retained per gram of superabsorbent cellulosic fiber and are expressed as free swell in the units of g/g. The free swell is determined in accordance with the equation below:

Free swell=[Weight of sample−(Weight of dry sample+Weight of teabag+Weight of liquid absorbed by blank]/Weight of dry sample.

The Absorbency Test Method

The absorbency test method was used to determine the absorbency under load and retention under load of the superabsorbent fibers of the present invention. The absorbency test was carried out in a one inch inside diameter plastic cylinder having a 100-mesh metal screen adhering to the cylinder bottom "cell," containing a plastic spacer disk having a 0.995 inch diameter and a weight of about 4.4 g. In this test, the weight of the cell containing the spacer disk was determined to the nearest 0.0001 g, and then the spacer was removed from the cylinder and about 0.35 g (dry weight basis) of superabsorbent fiber were air-laid into the cylinder. The spacer disk then was inserted back into the cylinder on the fiber, and the cylinder group was weighed to the nearest 0.0001 g. The fiber in the cell was compressed with a load of 4 psi for 60 seconds, the load then was removed and fiber pad was allowed to equilibrate for 60 seconds. The pad thickness was measured, and the result was used to calculate the dry bulk of the cross-linked fiber.

A load of 0.3 psi then was applied to the fiber pad by placing a 100 g weight on the top of the spacer disk, and the pad was allowed to equilibrate for 60 seconds, after which the pad thickness was measured. The cell and its contents then were hanged in a Petri dish containing a sufficient amount of saline solution (0.9% by weight saline) to touch the bottom of the cell. The cell was allowed to stand in the Petri dish for 10 minutes, and then it was removed and hanged in another empty Petri dish and allowed to drip for 30 seconds. The 100 g weight then was removed and the weight of the cell and contents was determined. The weight of the saline solution absorbed per gram fiber then was determined and expressed as the absorbency under load (gig). The cell containing the fiber was hanged again under zero load in the tray containing the saline solution. The cell was left in contact with the saline solution for 10 min. Then the 0.3 psi load was placed back into the cell over the fiber and the cell was left in contact with the saline solution for another 10 min. The 100 g weight was then removed and the weight of the cell and contents was determined. The weight of the saline solution absorbed per gram fiber then was determined and expressed as the retention under load (g/g).

The cell then was centrifuged for 3 min at 1400 rpm (Centrifuge Model HN, International Equipment Co., Needham HTS, USA), and weighed. The results obtained were used to calculate the weight of saline solution retained per gram fiber, and expressed as the centrifuge retention capacity (g/g).

Example 1

This example provides a representative method for making superabsorbent fiber of the present invention at high consistency.

A sample of never dried Rayfloc®-J-LD was obtained as a 33.7% solid wet lap from a Rayonier mill at Jesup, Ga., and is an untreated southern pine Kraft pulp sold by Rayonier Performance Fibers Division, Jesup, Ga. and Fernandina Beach, Fla. for use in products requiring good absorbency, such as absorbent cores in diapers. A 40.0 g (dry weight basis) sample was suspended in an aqueous solution (1.0 L, taking into consideration the amount of water present in the never dried pulp) of acrylic acid (180.0 g), and methylenebisacrylamide (5.0 g). The mixture was agitated for about 15 min, then excess liquid was removed by suction filtration (centrifuge, or mechanical pressing) to obtain a fiber with a pick-up of about 110.0 g. This pick-up affords about 20.0 g of acrylic acid and 0.55 g of methylenebisacrylamide on fiber. The treated fiber was charged in a 2 L Pyrex reaction kettle. The reaction kettle is fitted with a thermocouple inserted though a rubber septum, a Teflon bladed agitator on a glass shaft attached to a mechanical mixer, a gas inlet polyethylene tubing inserted through an adapter fitted with a rubber septum, and a gas outlet adapter connected to a gas trap partially filled with oil. The fiber in the reaction kettle was agitated and purged with nitrogen gas for at least 30 min to remove oxygen. Then, ammonium cerium (IV) nitrate solution (0.5 g in 100 mL, 0.1 N nitric acid) was added dropwise via a syringe. The final consistency of the reaction mixture was about 16%. The resulting reaction mixture was allowed to react at room temperature for about 10–20 min and then for about 1 h at 40° C. The resulting grafted fiber was then washed thoroughly by dispersing it in water (about 1 L) using a British disintegrater, and then filtered. The fiber then was neutralized to a pH of about 6 to 7 by agitating it for about 5 min in 1 L water containing sodium bicarbonate (4.0 g), using a British disintegrator. The resulting gel then was transferred to a plastic container (4 L) and diluted with acetone (2 L) to dehydrate and precipitate the fiber. The resulting fiber was then collected by suction filtration and air-dried to afford 57.0 g of dry fiber (85% grafting efficiency).

Example 2

A sample of never dried Porosanier-J, obtained as a 43.3% solid wet lap from a Rayonier mill at Jesup, Ga., (a mercerized fiber commercially available from the Rayonier mill at Jesup, Ga.). A 40.0 g (dry weight basis) sample was suspended in an aqueous solution (1.0 L, taking into consideration the amount of water present in the never dried pulp) of acrylic acid (180.0 g), and methylenebisacrylamide (5.0 g). The mixture was agitated for about 15 min, then excess liquid was removed by suction filtration (centrifuge, or mechanical pressing) to obtain a fiber with a pick-up of about 110.0 g. This pick-up affords about 20.0 g of acrylic acid and 0.55 g of methylenebisacrylamide on fiber. The treated fiber was charged in a 2 L Pyrex reaction kettle equipped as described in Example 1. The fiber in the reaction kettle was agitated and purged with nitrogen gas for at least 30 min to remove oxygen. Then pottasium persulfate (0.5 g in 100 mL distilled water) was added drop-wise via a syringe. The final consistency of the reaction mixture was about 16%. The resulting reaction mixture was allowed to react at room temperature for about 10–20 min and then for about 1 h at 70° C. The resulting grafted fiber was then washed thoroughly by dispersing it in water about 1 L using British disintegrator, then filtered. The fiber then was neutralized to a pH of about 6 to 7 by agitating it for about 5 min in a 1 L water containing sodium bicarbonate (4.0 g) using British disintegrator. The resulting gel was then transferred to a plastic container (4 L) and diluted with acetone (2 L) to dehydrate and precipitate the fiber. The resulting fiber was then collected by suction filtration and air-dried to afford 56.0 g of dry fiber (80% grafting efficiency).

Example 3

A sample of Porosanier-J Fiber (40.0 g) treated with acrylic acid and methylenbisacrylamid solution as described in example 1 was loaded in a horizontal high Parr reactor (Parr Instrument Company, Moline, Ill.). The reactor was connected to a vacuum pump, a cylinder of an inert gas, and to a high-pressure sample cylinder via Teflon tubing. The fiber in the reactor was degassed by pressurizing it using an inert gas such as $N_2$ and evacuating it using a vacuum pump for at least two times. An aqueous solution of an initiator described in Example 2 was added to the high pressure sample cylinder and degassed by pressurizing it using $N_2$ and evacuating it using vacuum pump. While the gas addition cylinder containing the initiator under a positive pressure and the Parr reactor containing the treated fiber under vacuum the initiator was added slowly to the fiber while being agitated. After the addition of the initiator solution was completed, the Parr reactor was pressurized to about 50 psi using carbon dioxide. The produced reaction mixture was agitated from 10 min at room temperature, the temperature was then increased to about 70° C. in about 30 min and maintained at 70° C. for 1 h. After about 1 h the reactor was cooled down to room temperature, fiber removed from the reactor then purified and neutralized as described in example 1 to produce 58.5 g of grafted fiber (92.5% grafting efficiency).

Figure 2:
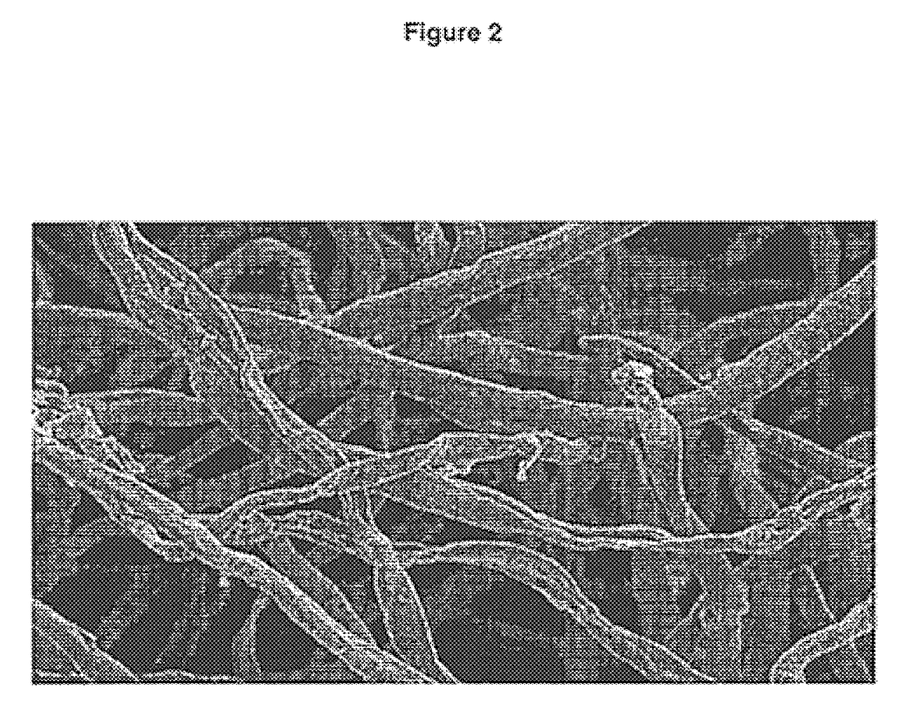
FIG. 2 is a scanning electron microscope (SEM) photograph of superabsorbent fibers of the present invention at 200× magnification.
Figure 3:
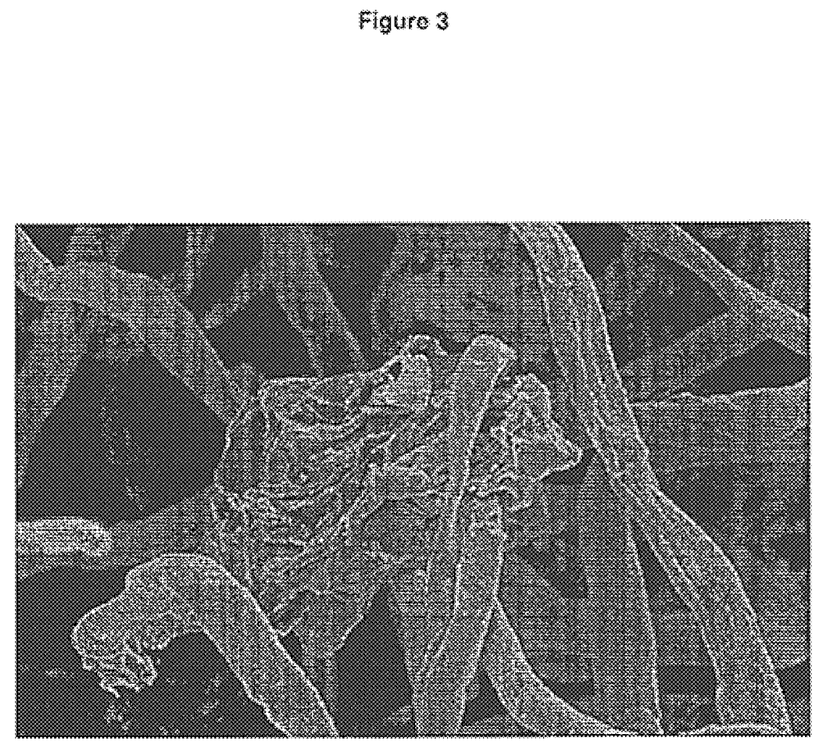
FIG. 3 is a scanning electron microscope (SEM) photograph of superabsorbent fibers of the present invention at 400× magnification. The fibers shown in FIGS. 2 and 3 are prepared according to Example 3.

Fibers prepared in accordance with Example 3 were examined under a scanning electron microscope (SEM) and 200×, and 400×photographs of the fibers were taken. These photographs are provided as FIGS. 2 and 3, respectively. Usually mercerized fibers (FIG. 1) have round circular shape as shown in FIG. 1. As shown in FIGS. 2 and 3, the fibers after grafting are twisted, curled, and have flat, ribbon-like shapes.

Example 4

Example 3 was repeated except that a mixture of cross-linking agents was used in this experiment. Fiber (40.0 g, dry weight basis) was suspended in an aqueous solution (1 L) of acrylic acid (180.0 g), methylenebisacrylamide (5.0 g), and glyceroldiglycidyl ether (3.0 g). The oven dried weight of grafted fiber was 59.0 g (95% grafting efficiency).

Example 5

Example 3 was repeated except that a mixture of cross-linking agents was used in this experiment. Fiber (40.0 g, dry weight basis) was suspended in an aqueous solution (1 L) of acrylic acid (180.0 g), methylenebisacrylamide (2.5 g), and 3-methacryloxypropyltrimethoxysilane (2.5 g). The oven dried weight of the grafted fiber was 58.6 g (93.0% grafting efficiency).

Example 6

This example illustrates a representative method for making superabsorbent fiber of the present invention at low consistency.

A 40.0 g (dry weight basis) sample of never dried Rayfloc®-J-LD at a consistency of about 33.7% was charged in a 2 L Pyrex reaction kettle. The reaction kettle was equipped as described in Example 1. To the fiber in the reaction kettle was added a saline solution (20%, 700 g) containing acrylic acid (20.0 g), methylenebisacrylamide (0.6 g). The mixture in the reaction kettle was agitated and purged with nitrogen gas for at least 30 min to remove oxygen. Then, potassium persulfate solution (0.5 g in 50 mL) was added drop-wise via a syringe to produce slurry with a total weight of about 800 g and a fiber consistency of about 5%. The resulting reaction mixture was allowed to react at room temperature for about 10–20 min, then at about 70° C. for about 1 h to insure complete reaction. After about 1 hour, the produced fiber was removed from the reaction kettle and thoroughly washed with water (3×1 L) to ensure complete removal of salt, unreacted monomers, and homopolymer. The fiber was then neutralized to a pH of about 6 to 7 with an aqueous solution of sodium bicarbonate (4.0 g in 1 L water). The resulting gel was transferred to a plastic container (4 L) and diluted with acetone (1 L) to dehydrate and precipitate the fiber. The resulting fiber then was collected by suction filtration and air-dried to yield 54.3 g of grafted fiber (71.5% grafting efficiency).

Example 7

A sample of never dried Rayfloc®-J-LD 40.0 g (dry weight basis) was suspended in an aqueous solution (1.0 L, taking into consideration the amount of water present in the never dried pulp) containing acrylic acid (90.0 g), methylenebisacrylamide (2.50 g), and salt (200.0 g). The mixture was agitated for about 15 min, then excess solution was removed by suction filtration to obtain fibers with a pick-up of about 220.0 g. This consistency affordeds about 20.0 g of acrylic acid and 0.55 g of methylenebisacrylamide on fiber. The treated fiber was loaded in a high Parr reactor and the reactor was degassed as described above in Example 3. An aqueous solution of the initiator potassium persulfate (0.5 g in 100.0 g) was loaded in a high pressure sample cylinder degassed and added to the fiber in the Parr reactor as described in Example 3. The produced slurry had a total weight of about 360.0 g, and a fiber consistency of about 11%. The slurry was agitated for about 10 min at room temperature, then the temperature was increased to 70° C. in about 30 min and maintained at 70° C. for 1 hour. After about 1 hour, the reactor was cooled down to room temperature, the fiber was removed from the reactor, and then washed and dried as described in Example 6 to produce 58.9 g of grafted fiber with a grafting efficiency of about 94.5%.

Example 8

A sample of never dried Porosanier-J, 40.0 g (dry weight sample) was loaded in the high Parr reactor described in Example 3. The fiber in the reactor was degassed by pressurizing it using an inert gas such as $N_2$ and evacuating it using a vacuum pump for at least two times. An aqueous solution (120 g) of acrylic acid (20.0 g) and methylenebisacrylamide (0.5 g) was loaded in the high pressure sample cylinder and a solution of potassium persulfate intiator (0.5 g in 100 ml $H_2O$) was loaded in another high pressure sample cylinder. Both cylinders were connected to the high Parr reactor via Teflon tubing. Both cylinders were then degassed by pressurizing and evacuating. The solution of acrylic acid and cross-linking agent was then added over about 5 min to the fiber while the fiber was under vacuum and being agitated, followed by addition of the solution containing the initiator. After the addition of the initiator solution was completed, the pressure in the Parr reactor was raised to about 50 psi. The produced reaction mixture was agitated at room temperature for about 10 min. Then, the temperature was increased to 70° C. in about 30 min and maintained at 70° C. for 1 hour. After about 1 hour, the reactor was cooled down to room temperature, the fiber was removed from the reactor, washed thoroughly with water, and neutralized to pH 6 to 7. The swollen fiber was then dehydrated using acetone as described in example 1 to afford about 59.3 g of grafted fiber with a grafting efficiency of about 96.5%.

Example 9

A sample of never dried Porosanier-J 40.0 g (dry weight sample) was shredded, then spread on a glass tray. An aqueous solution (120 g) of acrylic acid (20.0 g) and methylenebisacrylamide was sprayed evenly onto the fiber. The treated fiber was then loaded into the high Parr reactor and the reaction was carried out as described in Example 3. This procedure afforded 58.7 g of grafted fiber with a grafting efficiency of about 93.5%.

Example 10

Example 3 was repeated, except that the grafting was carried out using acetic acid as solvent in the place of water and the grafting was carried out onto never dried Rayfloc®-J-LD. The oven dried weight of grafted fiber is 59.5 g (90.3% grafting efficiency).

Example 11

Example 10 was repeated, except that the grafting was carried out on never dried Porosanier. The oven dried weight of grafted fiber is 59.1 g (93.5% grafting efficiency).

Example 12

This example shows the effect of using various amounts of acrylic acid on the free swell, centrifuge retention capacity, and absorbency under load of the superabsorbent fiber developed in the present invention as described in example 3 using Porosanier-J fiber. The results are summarized in Table 1.

TABLE 1

| Wt % of Acrylic acid on fiber[1] | Grafting efficiency (%) | Free swell (g/g) | Centrifuge Retention Capacity (g/g) | Absorbency under Load (g/g) | Retention Under Load (g/g) |
|---|---|---|---|---|---|
| 100.0 | >98.0 | 25.0 | 9.6 | 13.0 | 16.2 |
| 75.0 | 95.2 | 25.0 | 10.0 | 13.7 | 16.2 |
| 50.0 | 92.5 | 23.1 | 8.5 | 13.6 | 15.5 |
| 37.5 | 86.0 | 21.5 | 7.0 | 11.4 | 12.1 |
| 25.0 | 78.0 | 23.7 | 4.6 | 9.8 | 12.6 |

[1]Wt % of acrylic acid on fiber = (weight of acrylic acid added to fiber/weight of fiber) × 100.

Example 13

This example describes a wet-laid method for making a handsheet of superabsorbent fiber made in accordance with the present invention. A 12 inch×12 inch standard handsheet having a basis weight of about 500 g/m² was prepared using a 12 inch×12 inch wet-laid handsheet former mold, available from Adirondack Machine Corporation (Glens falls, N.Y.).

A British Disintegrator available from Testing Machine Incorporation (Amityville, N.Y.) was loaded with 46.5 g of superabsorbent fiber of the present invention, and to the fiber was then added 2.0 liters of an aqueous solution of acetone (60%). The suspension was mixed at 3000 rpm for about 5 min. The contents of the British disintegrator were then mixed with two more liters of an aqueous solution of acetone in a separate bucket. The whole mixture was then transferred to the handsheet former, mixed for about 30 sec, and then drained through the forming screen of the handsheet former. The sheet was then removed from the handsheet former, pressed to remove excess solution, and dried at room temperature or in an oven at temperature below 100° C.

Example 14

This example shows the effect of using various amounts of acrylic acid on the free swell, centrifuge retention capacity, absorbency under load, and retention under load of the superabsorbent fiber developed in the present invention as described in example 8 using Porosanier-J fiber and potassium persulfate (0.5 g in 100 mL $H_2O$) was used as an initiator. The results are summarized in Table 2.

TABLE 2

| Weight % Acrylic acid on fiber | Free swell (g/g) | Centrifuge Retention Capacity (g/g) | Absorbency under Load (g/g) | Retention Under Load (g/g) |
|---|---|---|---|---|
| 75.0 | 29.0 | 12.0 | 13.7 | 15.7 |
| 50.0 | 28.5 | 9.8 | 13.0 | 14.7 |
| 37.5 | | | 11.8 | 12.6 |
| 25.0 | 18.6 | 4.2 | 8.8 | 10.0 |

From Tables 1 and 2, it can be seen that the superabsorbent cellulosic fibers of the present invention have absorbent retention efficiencies within the range of from about 0.65 to about 0.99, and absorbency efficiencies within the range of from about 0.56 to about 0.95.

Example 15

This example illustrates an airlaid method for forming a representative absorbent core of the present invention.

An airlaid absorbent core formed in accordance with the present invention was prepared using an airlaid apparatus. Conventional fiber, superabsorbent fiber of the present invention, and superabsorbent polymer were loaded into the airlaid apparatus. Vacuum was then applied, the fibers and superabsorbent polymer travelled through plastic tubing and were combined through an air vortex into a plastic cylinder having a 200-mesh metal screen adhering to the cylinder bottom. The cylinder had an inside diameter of 60 mm and a height of 50 mm. After the fibers and superabsorbent polymer were completely used, the vacuum was discontinued and the resulting pad was removed from the cylinder. The pad had a diameter of about 60 mm and weighed about 3.0 g (basis weight 1061 g/m²). The pad was then compressed to a density of about 0.3 g/cm³ using a hydraulic press at a pressure of 700 psi for 10 sec. The pad was then used for further evaluation.

Example 16

In this example, the absorbency under load and absorbent capacity of representative absorbent cores formed in accordance with the present invention as described in example 15 were measured. The absorbent core was placed in a pre-weighed plastic cylinder (described in Example 15) containing a weight holder. The plastic weight holder was placed on top of the pad and a load of 0.6 PSI was placed on the weight holder. In a plastic tray, a glass fretted cylinder was placed with the smooth surface facing up and the coarse surface facing down. The cylinder had a diameter of about 120 mm and a thickness of about 9 mm. A black ribbon filter paper having a diameter of about 70 mm (Schleicher and Schnell, Dassel, Germany) was placed on the glass fretted cylinder in the center. Saline solution was added to the tray in an amount sufficient to reach the upper edge of the glass fretted cylinder. The plastic cylinder containing the pad under 0.6 PSI was then placed on top of the filter paper and allowed to stand in the tray for about 30 min. After about 30 min the plastic cylinder was removed from the tray, and the load was removed from the plastic cylinder. The weight of the plastic cylinder and its contents was then determined and the results were used to determine the absorbency under load. The plastic cylinder containing the core was returned to the tray containing the saline solution placed as described above on the glass fretted cylinder while under zero load and left in contact with saline solution for another 30 min. The weight of the cylinder and its contents was then determined and results used to calculate the absorbent capacity. The superabsorbent fiber used in the preparation of absorbent cores shown in Table 3 are made in accordance with present invention as shown in example 3.

TABLE 3

| Absorbent Core | | | Absorbency under Load | Absorbent |
| --- | --- | --- | --- | --- |
| Fluff (%) | Superabsorbent fiber (%) | Superabsorbent polymer (%) | (g saline/g) saline | Capacity (g saline/g) |
| 45 | | 55 | 12.4 | 22.4 |
| | 45 | 55 | 16.9 | 27.5 |
| | 55 | 45 | 15.7 | 25.6 |
| 40 | 20 | 40 | 14.1 | 22.1 |
| 10 | 60 | 30 | 12.0 | 20 |
| | 100 | | 9.9 | 15.7 |

The superabsorbent fiber of the present invention, when used in an absorbent core, provides improved absorbency ratios, whereby the absorbency ratio is AUL/Absorbent Capacity. The ratios reported in Table 3 range from about 0.55 for conventional SAP, to about 0.64 for the SAP fiber of the invention present in an amount of about 20%. Accordingly, for AUL values above about 8 for the absorbent core, the superabsorbent fibers of the present invention provide absorbency ratios of from about 0.56 to about 0.95.

The superabsorbent fiber used in the preparation of the absorbent cores shown in Table 4 are made in accordance with the present invention as described in example 3 using 37% by fiber weight acrylic acid.

TABLE 4

| Absorbent Core | | | Absorbency under Load | Absorbent |
| --- | --- | --- | --- | --- |
| Fluff (%) | Superabsorbent fiber (%) | Superabsorbent polymer (%) | (g saline/g) saline | Capacity (g saline/g) |
| 45 | | 55 | 12.4 | 22.4 |
| | 45 | 55 | 15.7 | 27.2 |
| | 55 | 45 | 14.2 | 25.0 |
| 30 | 45 | 25 | 12.4 | 19.0 |
| | 70 | 30 | 13.1 | 22.0 |
| 20 | 60 | 20 | 12.5 | 20.4 |
| | 100 | | 9.6 | 13.5 |

The superabsorbent fiber of the present invention, when used in an absorbent core, provides improved absorbency ratios, whereby the absorbency ratio is AUL/Absorbent Capacity. The ratios reported in Table 4 range from about 0.55 for conventional SAP, to about 0.71 for the SAP fiber of the invention. Accordingly, for AUL values above about 8 for the absorbent core, the superabsorbent fibers of the present invention provide absorbency rations of from about 0.56 to about 0.95.

Example 16

This example shows a comparison between the acquisition times of representative absorbent cores formed in accordance with the present invention as described above in example 14 using various amounts of superabsorbent fiber of the present invention, fluff, and commercial superabsorbent polymer.

The acquisition time was determined by SART test method. The test measures the time required for a dose of saline to be absorbed completely into the absorbent article. The test was conducted on an absorbent article consisting of absorbent core in pad form and an acquisition layer. The acquisition layer was a cross-linked fiber obtained from a commercially available diaper (Hüggies, from Kimberly-Clark Corporation, Neenah, Wis.).

In this test, the acquisition fiber was airlaid into a pad weighing about 0.7 g, and then was compressed with a load of 7.6 PSI for 60 seconds. The acquisition pad then was placed over the absorbent core and both were placed into a testing cell. The testing cell consisted of a plastic base and a funnel cup. The base was a plastic cylinder having an inside diameter of 60.0 mm used to hold the sample. The funnel cup was a plastic cylinder having a hole with a star shape, the outside diameter of the funnel cup was 58 mm, and it was placed inside the plastic base on top of the sample. A load of 0.6 PSI having a donut shape was placed on top of the funnel cup.

The cell and its contents were placed on a leveled surface and dosed with three successive insults, each insult being 9.0 mL of saline solution, the time interval between doses was 20 min. The doses were added with a Master Flex Pump (Cole Parmer Instrument, Barrington, Ill., USA) to the funnel cup, and the time in seconds required for the saline solution of each dose to disappear from the funnel cup was recorded as the acquisition time. The results are provided in Table 5 below.

TABLE 5

| Absorbent Core | | | Acquisition time | | |
| --- | --- | --- | --- | --- | --- |
| | | | $1^{st}$ | $2^{nd}$ | $3^{rd}$ |
| Fluff % | Superabsorbent fiber (%) | Superabsorbent polymer (%)[3] | Insult (sec) | Insult (sec) | Insult (sec) |
| 45 | | 55 | 3.9 | 8.9 | 16.8 |
| 20 | 60[1] | 20 | 4.1 | 11.4 | 14.9 |
| 20 | 60[2] | 20 | 3.2 | 9.5 | 10.5 |
| | 80 | 20 | 6.2 | 17.9 | 18.7 |

[1]Superabsorbent fiber from Example 3, using 37% acrylic acid based on fiber weight.
[2]Superabsorbent fiber from Example 3, using 100% acrylic acid based on fiber weight.
[3]Obtained from BASF (P-02-055-01).

The superabsorbent fibers of the present invention, when incorporated into an absorbent core, provide improved third insult acquisition times. When compared to conventional SAP alone, the fibers of the invention can effectively reduce the third insult acquisition time significantly when used in amounts on the order of about 60%.

While the present invention has been described in detail with reference to particularly preferred embodiments and examples, those skilled in the art will appreciate that various modifications may be made to the invention without departing from the spirit and scope thereof.

What is claimed is:

1. A superabsorbent cellulosic fiber comprising cellulose and at least one ethylenically unsaturated monomer grafted to the cellulose, whereby the superabsorbent cellulosic fiber has a a cross linking density of less than about 20%.

2. The superabsorbent fiber of claim 1, wherein the fibers have a dry density of at least about 0.04 g/cm$^3$.

3. The superabsorbent fiber of claim 1, wherein the fibers have a centrifuge retention of more than about 4 g saline/g fiber.

4. The superabsorbent fiber of claim 1, wherein the fibers have a free swell of at least about 10 g saline/g fiber.

5. The superabsorbent fiber of claim 1, wherein the fibers have a grafting efficiency of greater than about 85%.

6. A superabsorbent fiber comprising cellulose and at least one ethylenically unsaturated monomer grafted to the cellulose, whereby the superabsorbent cellulose fiber has a grafting efficiency of greater than about 75%, and wherein when the superabsorbent fiber is incorporated into an absorbent core, the absorbent core has a third insult acquisition time of less than about 25 seconds.

7. The superabsorbent fiber of claim 1, wherein superabsorbent fiber has an absorbent retention efficiency of from about 0.65 to about 0.99, the absorbent retention efficiency being represented by the following equation:

Absorbent retention efficiency (%)=Absorbency Under Load/Retention Under Load×100.

8. The superabsorbent fiber of claim 1, wherein when the superabsorbent fiber is incorporated into an absorbent core, the absorbent core has an absorbency efficiency of from about 0.56 to about 0.95, the absorbency efficiency being represented by the following equation:

Absorbency efficiency (%)=Absorbency Under Load/Absorbent Capacity×100.

9. The superabsorbent fiber of claim 1, wherein the cellulosic fiber is a fiber treated with at least 4% caustic solution.

10. The superabsorbent fiber of claim 1, wherein the ethylenically unsaturated monomer is one or more monomers having the formula:

where R represents hydrogen, methyl, or ethyl.

11. The superabsorbent fiber of claim 10, wherein the ethylenically unsaturated monomer is one or more monomers selected from the group consisting of acrylic acid, methacrylic acid, ethacrylic acid, α-chloroacrylic acid, α-cyanoacrylic acid, vinylsulfonic acid, acryamidopropane-sulfonic acid, crotonic acid, α-acryloxypropionic acid, sorbic acid, isocrotonic acid and alkali metal salts of itaconic acid, and ammonium salts, and mixtures thereof.

12. The superabsorbent fiber of claim 11, wherein the ethylenically unsaturated monomer is one or more monomers selected from the group consisting of acrylic acid, methacrylic acid, and mixtures thereof.

13. A superabsorbent fiber prepared by contacting a cellulosic fiber with one or more ethylenically unsaturated monomers, whereby the superabsorbent cellulosic fiber has a cross-linking density of less than about 20%.

14. The superabsorbent fiber of claim 13, wherein the cellulosic fiber is contacted with one or more ethylenically unsaturated monomers in the presence of a cross-linking agent.

15. The superabsorbent fiber of claim 14, wherein the cross-linking agent includes polyfunctional groups capable of polymerizing in the presence of a free radical initiator, or optionally capable of reacting with carboxyl and hydroxy groups of the neighboring monomers simultaneously.

16. The superabsorbent fiber of claim 15, wherein the cross-linking agent is selected from the group consisting of diacrylates and dimethacrylates of ethylene glycol, bisacrylamides, epoxy acrylates, allyamines, polyepoxides, epoxy silanes, methacryloxy or acryloxy silanes, aminosilanes, and mixtures thereof.

17. The superabsorbent fiber of claim 16, wherein the cross-linking agent is a mixture of a bisacrylamide and at least one of polyepoxides or methacryloxy silanes.

18. The superabsorbent fiber of claim 13, wherein the fiber is further prepared in the presence of a free radical initiator.

19. The superabsorbent fiber of claim 18, wherein the free radical initiator is selected from the group consisting of potassium persulfate, ammonium persulfate, sodium persulfate, alkali-metal persulfates, hydrogen peroxide, ammonium cerium nitrate, 2,2'-azobis-(2-amidinopropane) hydrochloride, and mixtures thereof.

20. The superabsorbent fiber of claim 13, whereby the fiber has a grafting efficiency of ethylenically unsaturated monomer on cellulose of greater than about 85%.

21. The superabsorbent fiber of claim 13, wherein the fibers have a dry density of at least about 0.04 g/cm$^3$.

22. The superabsorbent fiber of claim 13, wherein the fibers have a centrifuge retention of more than about 4 g saline/g fiber.

23. The superabsorbent fiber of claim 13, wherein the fibers have a free swell of at least about 10 g saline/g fiber.

24. The superabsorbent fiber of claim 13, wherein the fibers have a grafting efficiency of greater than about 95%.

25. A superabsorbent fiber comprising cellulose and at least one ethylenically unsaturated monomer grafted to the cellulose, whereby the superabsorbent cellulosic fiber has a grafting efficiency of greater than about 75%, and prepared by contacting a cellulosic fiber with one or more ethylenically unsaturated monomers, wherein when the superabsorbent fiber is incorporated into an absorbent core, the absorbent core has a third insult acquisition time of less than about 25 seconds.

26. The superabsorbent fiber of claim 13, wherein superabsorbent fiber has an absorbent retention efficiency of from about 0.65 to about 0.99, the absorbent retention efficiency being represented by the following equation:

Absorbent retention efficiency (%)=Absorbency Under Load/Retention Under Load×100.

27. The superabsorbent fiber of claim 13, wherein the superabsorbent fiber an absorbency efficiency of from about 0.56 to about 0.95, the absorbency efficiency being represented by the following equation:

Absorbency efficiency (%)=Absorbency Under Load/Absorbent Capacity×100.

28. An absorbent article comprising the superabsorbent fiber of claim 1.

29. The absorbent article of claim 28, wherein the absorbent article is at least one article selected from the group consisting of infant diapers, feminine care products, training pants, and adult incontinence briefs.

30. The absorbent article of claim 28 comprising a liquid penetrable top sheet, a liquid impenetrable back sheet, an acquisition layer, and an absorbent core, wherein the acquisition layer is disposed beneath the top sheet, and the absorbent core is disposed between the acquisition layer and the back sheet.

31. The absorbent article of claim 30, wherein the acquisition layer comprises the superabsorbent fiber.

32. The absorbent article of claim 30, wherein the absorbent core comprises a composite of superabsorbent polymer and the superabsorbent cellulosic fiber.

33. The absorbent article of claim 32, wherein the superabsorbent polymer is selected from the group consisting of polyacrylate polymers, starch graft copolymers, cellulose graft copolymers, cross-linked carboxymethylcellulose derivatives, and mixtures and combinations thereof.

34. The absorbent article of claim 32, wherein the superabsorbent polymer is in the form of fiber, flakes, or granules.

35. The absorbent article of claim 32, wherein the superabsorbent cellulose fiber is present in an amount of from about 20 to about 80% by weight, based on the total weight of the absorbent structure.

36. The absorbent article of claim 32, further comprising cellulosic fiber in addition to the superabsorbent cellulose fiber.

37. The absorbent article of claim 36, wherein the cellulosic fiber is a wood pulp fiber selected from the group consisting of hardwood pulp, softwood cellulose pulp obtained from a Kraft or sulfite chemical process, caustic treated wood pulp, rayon, cotton linters, and combinations or mixtures thereof.

38. The absorbent article of claim 36, wherein the absorbent core comprises about 60% superabsorbent cellulosic fiber, about 20% cellulosic fiber, and about 20% by weight superabsorbent polymer, based on the weight of the absorbent core.

39. The absorbent article of claim 30, wherein the absorbent site of cellulosic fiber and the superabsorbent cellulosic fiber.

* * * * *